United States Patent [19]

Skotnicki et al.

[11] Patent Number: 4,751,305

[45] Date of Patent: Jun. 14, 1988

[54] 2-HETEROCYCLOBENZO[B][1,6]NAPH-THYRIDINES AS INHIBITORS OF INTERLEUKIN

[75] Inventors: Jerauld S. Skotnicki, Chadds Ford; Steven C. Gillman, Newtown Square, both of Pa.

[73] Assignee: American Home Products Corporation, New York, N.Y.

[21] Appl. No.: 48,099

[22] Filed: May 7, 1987

[51] Int. Cl.$^4$ .................. C07D 401/04; C07D 413/04; C07D 471/04

[52] U.S. Cl. .................................... 544/331; 544/126; 544/238; 544/321; 544/324; 544/353; 544/354; 544/355; 544/356; 544/361; 544/405; 544/284; 546/81

[58] Field of Search .................. 546/81; 544/126, 238, 544/253, 333, 349, 361, 405, 284, 331, 353, 354, 355, 356, 321, 324

[56] References Cited

U.S. PATENT DOCUMENTS

| | | | |
|---|---|---|---|
| 3,637,706 | 1/1972 | Wolf et al. | 544/361 |
| 3,647,800 | 3/1972 | Wolf et al. | 546/81 |
| 3,674,790 | 7/1972 | Wolf et al. | 546/81 |

Primary Examiner—John M. Ford
Assistant Examiner—Zinna Northington
Attorney, Agent, or Firm—George Tanowski

[57] ABSTRACT

There are disclosed compounds of the formula

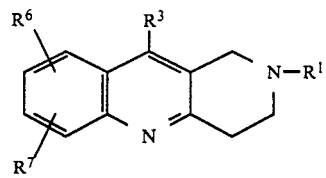

wherein $R^1$ is pyridl, quinolinyl, pyrazinyl, pyridinyl, pyridazinyl, pyrimidinyl, quinoxalinyl, quinazolinyl or any of the foregoing substituted with halo, lower alkyl, lower alkyl carbonyl, benzoyl, carboxy, lower alkoxycarbonyl, $OR^2$, $N(R^2)_2$, $CON(R^2)_2$, $SO_3R^2$, $SO_2N(R^2)_2$, phenylsulfonyl, lower alkylsulfonyl, cyano, nitro or trifluoromethyl;

$R^2$ is hydrogen, lower alkyl or phenyl;

$R^3$ is halo, morpholino, 4-methylpiperazino, $R^4NNHR^5$, $NR^4R^5$, $OR^5$, $SR^5$, $R^4NCH_2CH_2OCH_3$, $SCH_2CH_2CH_2NH_2$, or

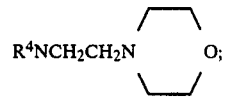

$R^4$ is hydrogen or lower alkyl;

$R^5$ is hydrogen, lower alkyl, lower alkanoyl, lower cycloalkylor phenyl; and $R^6$ and $R^7$ are each independently, hydrogen, halo, nitro, lower alkoxy, lower alkyl, cyano, trifluoromethyl, phenyl, carboxy or lower alkoxycarbonyl;

which, by virtue of their ability to inhibit interleukin 1, are of use as antiinflammatory agents and in treatment of disease states involving enzymatic tissue destruction, and are also intermediates in the preparation of other compounds which possess identical activities.

5 Claims, No Drawings

2-HETEROCYCLOBENZO[B][1,6]NAPHTHYRIDINES AS INHIBITORS OF INTERLEUKIN

This invention relates to novel compounds possessing interleukin 1 (IL 1) antagonist activity and having antiinflammatory activity.

Interleukin 1 (IL 1) is a peptide hormone exhibiting a number of immune and inflammatory actions [Dinarello, *Rev. Inf. Dis.* 6, 51 (1984)]. IL 1 is produced, in response to inflammatory stimuli, by leukocytes such as macrophages and polymorphonuclear cells, as well as by a variety of other cell types such as synovial cells, endothelial cells and keratinocytes, and it mediates several biological responses of leukocytes on other tissue targets such as bone, articular joints, liver, hypothalamus, and brain.

IL 1 was originally shown to augment the proliferation of T lymphocytes for which it was named lymphocyte activating factor (LAF), and is believed to be important for the generation of T cell-dependent immune responses.

There is evidence to suggest a relationship between IL 1 and pathology in various diseases, particularly immunoinflammatory disorders such as rheumatoid arthritis [Dinarello et al., *Ann. Rev. Med.* 37, 173 (1986)]. IL 1 induces acute inflammatory responses producing soft tissue swelling (edema and erythema) [Granstein et al., *J. Clin. Invest.*, 77, 1010 (1986)]. It is a chemoattractant for polymorphonuclear leukocytes (PMN) and induces the activation and migration of these cells into tissues. IL 1 also stimultates the production of prostaglandin $E_2$, a potent inflammatory arachidonic acid metabolite, by a variety of cells and tissues including chondrocytes and synovial cells [Mizel et al., *Proc. Nat'l. Acad. Sci.*, 78, 2474 (1981) and Chang et al., *J. Immunol.*, 136, 1283 (1986)] and hypothalamic tissue. This effect on the hypothalamus is thought to be responsible for fever production. IL 1 can induce articular joint destruction by stimulating the production of a variety of hydrolytic enzymes (neutral proteases such as collagenase, glycosaminoglycanases, etc.) which degrade cartilage matrix proteins (collagen, proteoglycan, etc.) by synovial cells, chondrocytes, and fibroblasts [Dayer et al., *Science*, 195, 181 (1977) and Postlethwaite et al., *J. Exp. Med.*, 157, 801 (1983)]. Furthermore, IL 1 induces hyperproliferation of dermal and synovial fibroblasts and is a potent inducer of bone resorption [Wood et al., *J. Immunol.*, 134, 895 (1985) and Gilman and Kimball, *Agents and Actions*, 16, 468 (1985)].

Finally, IL 1 mediates acute phase reactions including alterations in plasma divalent cations, increased synthesis by liver cells of acute phase proteins (C-reactive protein, serum amyloid A, etc.) and fever. Accordingly, compounds which have IL 1 antagonist activity and thereby inhibit the biological effects of IL 1 can be advantageously used to block pathologies in which one or more of these events occur such as rheumatoid arthritis, osteoarthritis and related disorders [Rodnan and Schumacher, eds, "Primer on the Arthritic Diseases" 8 ed. Atlanta, 1983], psoriasis and other inflammatory/proliferative skin disorders as well as diseases in which the secretion of collagenase (and other tissue hydrolysing neutral proteinases) had been implicated as a causative factor, including periodontal disease, tumor invasiveness, and epidermolysis bullosa [Perez-Tamayo, *Amer. J. Pathol.*, 92, 509 (1978) and Harris and Krane, *N. Engl. J. Med.*, 291, 652 (1974)] and so forth.

It has now been found that certain novel 2-heterocyclobenzo[b][1,6]naphthyridines antagonize the activity of IL 1, and so are useful as antiinflammatory agents and in the treatment of pathologies whose etiology is collagenase-based tissue destruction. The present invention provides novel compounds having the formula:

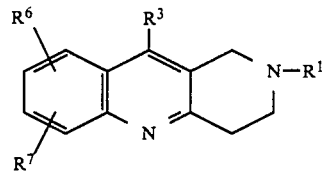

wherein
$R^1$ is pyridyl, quinolinyl, pyrazinyl, pyridinyl, pyridazinyl, pyrimidinyl, quinoxalinyl, quinazolinyl or any of the foregoing substituted with halo, lower alkyl, lower alkyl carbonyl, benzoyl, carboxy, lower alkoxycarbonyl, $OR^2$, $N(R^2)_2$, $CON(R^2)_2$, $SO_3R^2$, $SO_2N(R^2)_2$, phenylsulfonyl, lower alkylsulfonyl, cyano, nitro or trifluoromethyl;
$R^2$ is hydrogen, lower alkyl or phenyl;
$R^3$ is halo, morpholino, 4-methylpiperazino, $R^4NNHR^5$, $NR^4R^5$, $OR^5$, $SR^5$, $R^4NCH_2CH_2OCH_3$, $SCH_2CH_2CH_2NH_2$ or

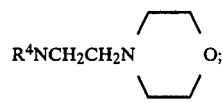

$R^4$ is hydrogen or lower alkyl;
$R^5$ is hydrogen, lower alkyl, lower alkanoyl, lower cycloalkyl or phenyl; and
$R^6$ and $R^7$ are each independently, hydrogen, halo, nitro, lower alkoxy, lower alkyl, cyano, trifluoromethyl, phenyl, carboxy or lower alkoxycarbonyl.

The terms "lower alkyl" and "lower alkoxy" refer to moieties having 1 to 6 carbon atoms in the carbon chain. The term "lower alkanoyl" refers to the moiety RCO— wherein R is an alkyl group having 1 to 6 carbon atoms. The term "lowercycloalkyl" refers to a saturated ring having 4 to 7 carbon atoms. The term "halo" refers to fluoro, chloro and bromo.

The compounds of the invention, in addition to possessing IL 1 antagonist activity, are also intermediates for producing certain of the compounds among those embraced by the formula

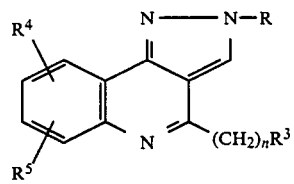

wherein
R is lower alkyl, carboxy lower alkyl, alkoxy carbonyl lower alkyl, cyano lower alkyl, nitro lower alkyl, hydroxy lower alkyl, lower alkoxy lower alkyl, $COR^1$, $CO_2R^2$, $CON(R^2)_2$, $SO_2R^1$, phenyl, naphthyl, pyridyl, quinolinyl or phenyl, naphthyl, pyridyl or quinolinyl substituted by halo, lower alkyl, lower alkoxy, nitro, cyano, amino, mono-lower alkyl amino, di-lower alkyl amino, carboxy, lower alkoxycarbonyl or hydroxy;

$R^1$ is phenyl, phenyl lower alkyl, naphthyl, pyridyl, quinolinyl, pyrazinyl, pyridinyl, pyrimidinyl, pyridazinyl, quinoxalinyl, quinazolinyl or any of the foregoing substituted with halo, lower alkyl, carboxy, cyano, nitro, lower alkylsulfonyl, lower alkoxy carbonyl or lower alkyl substituted by fluoro, carboxy, cyano, nitro or lower alkoxy carbonyl;

$R^2$ is hydrogen, lower alkyl, phenyl or benzyl;

$R^3$ is hydrogen, $R^1$, $OR^1$, $SR^1$, $NR^2R^1$, $NH_2$, $NR^6R^1$ or $NR^6R^7$;

$R^4$ and $R^5$ are each independently, hydrogen, halo, lower alkoxy, lower alkyl, trifluoromethyl, cyano, nitro, carboxy or lower alkoxycarbonyl;

$R^6$ is carbamoyl, phenylcarbamoyl, or halophenylcarbamoyl;

$R^7$ is hydrogen or lower alkyl; and n is 1–5.

The compounds of the invention can be prepared by the reaction of 1,4-dioxa-8-azaspiro[4.5]decane with a suitable halo-$R^1$ reactant, and following ketal hydrolysis, the reaction of the resultant intermediate with a suitably substituted amino benzoic acid in the presence of a halogenating agent to yield an intermediate halogenated benzo[b][1,6]naphthyridine:

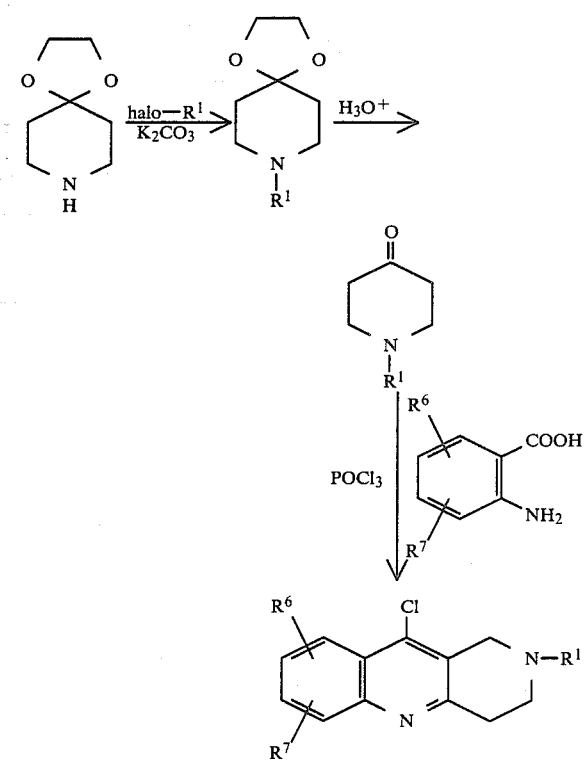

In the final step, the intermediate halogenated benzo[b][1,6]naphthyridine is reacted with a suitably substituted $R^3$-containing reactant to yield the desired final product:

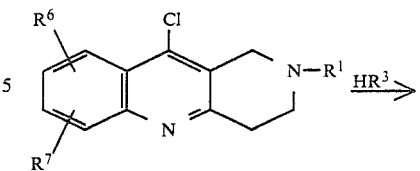

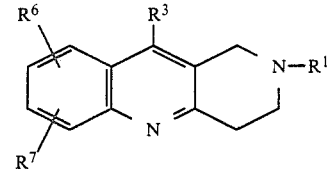

The starting materials used in the above outlined preparative sequences are all available commercially or can be prepared by conventional methods disclosed in the chemical literature.

The compounds of the invention, by virtue of the ability to antagonize interleukin 1, are useful in the treatment of such diseases as rheumatoid arthritis, osteoarthritis, tendinitis, bursitis and similar conditions involving inflammation, as well as psoriasis and other inflammatory/proliferative skin disorders. Moreover, the compounds are useful in treating disease states involving enzymatic tissue destruction, for example, conditions in which collagenase has been implicated as a causative factor, such as rheumatoid arthritis joint destruction, periodontal disease, tumor invasiveness, corneal ulcerations, epidermolysis bullosa and the like.

When the compounds of the invention are employed as antiinflammatory agents, or collagenase inhibitors, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic. For topical administration, the compounds may be formulated in the form of dusting powders, solutions, creams, lotions or aerosols in pharmaceutically acceptable vehicles, which are applied to affected portions of the skin.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The interleukin 1 antagonist activity, as well as the antiinflammatory effects of the compounds of the invention may be demonstrated by standard pharmacological procedures, which are described more fully in the examples given hereinafter.

These procedures illustrate the ability of the compounds of the invention to inhibit the IL 1-induced release of neutral protease from articular chondrocytes.

The following examples show the preparation and pharmacological testing of compounds within the invention.

EXAMPLE 1

7,10-Dichloro-1,2,3,4-tetrahydro-2-(2-pyrimidinyl)benzo[b][1,6]naphthyridine

A. 8-(2-Pyrimidinyl)-1,4-dioxa-8-azaspiro[4.5]decane

A mixture of 10 g (0.0873 mol) of 2-chloropyrimidine, 38 g (0.2654 mol) of 1,4-dioxa-8-azaspiro[4.5]decane, 18 g (0.130 mol) of $K_2CO_3$, and 100 ml of dimethylformamide is stirred at 100°–110° C. for 4 days. The reaction mixture is allowed to cool to ambient temperature, diluted with water and extracted with ethyl acetate. The combined organic extracts are washed copiously with water, then brine, dried over $Na_2SO_4$, and concentrated in vacuo to give a waxy solid. Trituration with ether furnishes 9.25 g (48%) of title compound: IR (KBr) 1670 and 1585 cm$^{-1}$; NMR (CDCl$_3$) δ8.30 (t, 1H), 6.46 (d, 2H), 4.02 (s, 4H), 3.98–3.88 (m, 4H), and 1.90–1.66 (m, 4H).

B. 1-(2-Pyrimidinyl)-4-piperidinone

A mixture of 8 g (0.036 mol) of the ketal of step A, above, 80 ml of 10% sulfuric acid solution, and 40 ml of tetrahydrofuran is stirred at ambient temperature for 3 days. The reaction mixture is diluted with water, basified with 2N sodium hydroxide solution and extracted with methylene chloride. The combined organic extracts are dried over $Na_2SO_4$ and concentrated in vacuo to give a waxy solid. Trituration with ether affords 2.9 g (45%) of title compound: IR (KBr) 1710 and 1585 cm$^{-1}$; NMR (CDCl$_3$) δ8.36 (d, 1H), 7.6 (t, 2H), 4.30–4.08 (m, 4H), and 2.62–2.46 (m, 4H).

C. 7,10-Dichloro-1,2,3,4-tetrahydro-2-(2-pyrimidinyl)benzo[b][1,6]naphthyridine

To a slurry of 16.75 g (0.0976 mol) of 2-amino-4-chlorobenzoic acid and 81.88 ml of phosphorous oxychloride is added portionwise 17.3 g (0.0976 mol) of the compound of step B, above. The mixture is stirred under reflux for 3 hours and then concentrated in vacuo. The residue is dissolved in chloroform and slowly added to an ice-$NH_4OH$ mixture. The mixture is stirred for 30 minutes and extracted with chloroform. The combined extracts are washed with brine, dried over $Na_2SO_4$, and concentrated in vacuo to yield 32.49 g of solid. Purification by HPLC and recrystallization from benzene furnishes 2.26 g (7%) of title compound as a pink solid: m.p. 172°–174° C.; IR (KBr) 1587 and 1465 cm$^{-1}$; NMR (CDCl$_3$) δ8.46 (d, 2H), 8.19 (d, 1H), 8.07 (s, 1H), 7.58 (m, 1H), 6.62 (t, 1H), 5.22 (s, 2H), 4.29 (t, 2H), 3.31 (t, 2H).

Analysis for: $C_{16}H_{12}Cl_2N_4$: Calculated: C, 58.02; H, 3.65; N, 16.92. Found: C, 58.05; H, 3.72; N, 16.70.

EXAMPLE 2

7,10-Dichloro-1,2,3,4-tetrahydro-2-(2-pyrazinyl)benzo[b][1,6]naphthyridine

A. 1-[2-Pyrazinyl]-4-piperidinone

A mixture of 20 g (0.1746 mol) of chloropyrazine, 36 g (0.260 mol) of $K_2CO_3$, 76 g (0.5308 mol) of 1,4-dioxa-8-azaspiro[4.5]decane, and 80 ml of dimethylformamide is stirred at 100° C. for 3 days. The reaction mixture is cooled, siluted with water, and extracted with ethyl acetate. The combined extracts are washed with water, dried over $Na_2SO_4$ and concentrated in vacuo. The residue, 400 ml of 10% sulfuric acid solution and 100 ml of tetrahydrofuran is stirred at ambient temperature for 4 days, diluted with water, basified with sodium hydroxide and extracted with methylene chloride. The extracts are washed with brine, dried over $Na_2SO_4$, and concentrated in vacuo. Trituration with ether gives 8.4 g of title compound: IR (KBr) 1720 and 1580 cm$^{-1}$; NMR (CDCl$_3$) δ8.24–7.88 (m, 3H), 3.98 (t, 4H), and 2.56 (t, 4H).

B. 7,10-Dichloro-1,2,3,4-tetrahydro-2-(2-pyrazinyl)benzo[b][1,6]naphthyridine

To a slurry of 20.24 g (0.118 mol) of 2-amino-4-chlorobenzoic acid and 100 ml of phosphorous oxychloride is added slowly 20.9 g (0.118 mol) of the compound of step A, above. The mixture is stirred under reflux for 3 hours and concentrated in vacuo. The residue is dissolved in chloroform, poured into an ice-$NH_4OH$ mixture, and stirred for 30 minutes. The mixture is extracted with chloroform. The combined extracts are washed with brine, dried over $Na_2SO_4$, and concentrated in vacuo to yield 40 g of solid. Purification by HPLC affords 3.1 g (8%) of title compound as a white solid: m.p. 182°–184° C. (dec.); IR (KBr) 1612, 1574, and 1479 cm$^{-1}$; NMR (CDCl$_3$) δ8.37 (s, 1H), 8.20 (m, 2H), 8.08 (s, 1H), 7.98 (s, 1H); 7.59 (m, 1H), 5.02 (s, 2H), 4.11 (t, 2H), 3.37 (t, 2H).

Analysis for: $C_{16}H_{12}Cl_2N_4$: Calculated: C, 58.02; H, 3.65; N, 16.92. Found: C, 57.93; H, 3.73; N, 16.50.

EXAMPLE 3

7,10-Dichloro-1,2,3,4-tetrahydro-2-(2-quinolyl)benzo[b][1,6]naphthyridine

A. 8-(2-Quinolinyl)-1,4-dioxa-8-azaspiro[4.5]decane

A mixture of 10 g (0.0613 mol) of 2-chloroquinoline, 27 g (0.1886 mol) of 1,4-dioxa-8-azaspiro[4.5]decane, 13 g (0.0941 mol) of $K_2CO_3$, and 75 ml of dimethylformamide is stirred at 100°–110° C. for 4 days. The reaction mixture is allowed to cool to ambient temperature, diluted with water and extracted with ethyl acetate. The combined organic extracts are washed copiously with water, then brine, dried over $Na_2SO_4$, and concentrated in vacuo to give a waxy solid. Trituration with ether furnishes 3.6 g (22%) of title compound: IR (KBr) 1620, 1610 and 1510 cm$^{-1}$; NMR (CDCl$_3$) δ7.92 (d, 1H), 7.78–7.50 (m, 3H), 7.30–7.22 (m, 1H), 7.04 (d, 1H), 4.02 (s, 4H), 3.94–3.86 (m, 4H), and 1.88–1.76 (m, 4H).

B. 1-(2-Quinolinyl)-4-piperidinone

A mixture of 3 g (0.011 mol) of the ketal of step A, above, 30 ml of 10% sulfuric acid solution, and 15 ml of tetrahydrofuran is stirred at ambient temperature for 4 days. The reaction mixture is diluted with water, basified using 2N sodium hydroxide solution, and extracted with methylene chloride. The combined organic extracts are dried over Na$_2$SO$_4$ and concentrated in vacuo to give a waxy solid. Trituration with ether furnishes 1.3 g (52%) of title compound: IR (KBr) 1710, 1610 and 1600 cm$^{-1}$; NMR (CDCl$_3$) δ7.96 (d, 1H), 7.80–7.18 (m, 4H), 7.04 (d, 1H), 4.16–4.02 (m, 4H), and 2.66–2.50 (m, 4H).

C.
7,10-Dichloro-1,2,3,4-tetrahydro-2-(2-quinolinyl)benzo[b][1,6]naphthyridine To a slurry of 9.1 g (0.053 mol) of 2-amino-4-chlorobenzoic acid and 45 ml of phosphorous oxychloride is added portionwise 12 g (0.053 mol) of the compound of step B, above. The mixture is stirred under reflux for 2½ hours and then concentrated in vacuo. The residue is taken up in chloroform and slowly added to an ice-NH$_4$ mixture. The mixture is stirred for 30 minutes before being extracted with chloroform. The combined extracts are washed with brine, dried over Na$_2$SO$_4$, and concentrated in vacuo to yield 24.55 g of solid. Purification by HPLC and recrystallization from benzene affords 6.65 g (33%) of title compound as an off-white solid: m.p. 160°–162° C.; IR (KBr) 1602 and 1508 cm$^{-1}$; NMR (CDCl$_3$) δ8.19 (d, 1H), 8.03 (m, 2H), 7.84 (br, 1H), 7.62 (m, 3H), 7.30 (m, 1H), 7.17 (d, 1H), 5.18 (s, 2H), 4.22 (t, 2H), 3.36 (t, 2H).

Analysis for: C$_{21}$H$_{15}$Cl$_2$N$_3$: Calculated: C, 66.33; H, 3.98; N, 11.05. Found: C, 66.72; H, 4.02; N, 10.86.

EXAMPLE 4
6-(7,10-Dichloro-3,4-dihydrobenzo[b][1,6]naphthyridin-2(1H)-yl-3-pyridinecarbonitrile, hemihydrate

A.
6-(1,4-Dioxa-8-azaspiro[4.5]decan-8-yl)-3-pyridinecarbonitrile, one quarter hydrate A mixture of 14 g (0.101 mol) 6-chloronicotinonitrile, 43 g (0.30) of 1,4-dioxa-8-azaspiro[4.5]decane, 22 g (0.159 mol) of K$_2$CO$_3$, and 100 ml of acetonitrile is stirred at reflux for four days. The reaction mixture is allowed to cool to ambient temperature, diluted with water and extracted with methylene chloride. The combined extracts are washed with brine, dried over Na$_2$SO$_4$, and concentrated in vacuo to give a pasty solid. Trituration with ether furnishes 24.3 g (98%) of title compound: IR (KBr) 2200, 1590, and 1490 cm$^{-1}$; NMR(CDCL$_3$) δ8.4 (m, 1H), 7.6 (m, 1H), 4.0 (s, 4H), 3.8(m, 4H), and 1.75 (m, 4H).

Analysis for: C$_{13}$H$_{15}$N$_3$O$_2$.¼H$_2$O:
Calculated: C, 62.50; H, 6.26; N, 16.82.
Found: C, 62.73; H, 6.06; N, 16.65.

B. 6-(4-Oxo-1-piperidinyl)-3-pyridinecarbonitrile

A mixture of 23 g (0.0942 mol) of the ketal of A, above, 500 ml of 10% sulfuric acid solution, and 250 ml of tetrahydrofuran is stirred at ambient temperature for 5 days. The reaction mixture is diluted with water and extracted with methylene chloride. The combined organic extracts are dried over Na$_2$SO$_4$ and concentrated in vacuo to give a pasty solid. Trituration with ether provides 14.2 g (75%) of title compound: IR(KBr) 2200, 1710, 1600, and 1500 cm$^{-1}$; NMR (CDCl$_3$) δ 8.45 (m, 1H), 7.67 (m, 1H), 6.7 (m, 1H), 4.03 (t, 4H) and 2.57 (t, 4H).

Analysis for: C$_{11}$H$_{11}$N$_3$O:
Calculated: C, 65.66; H, 5.51; N, 20.88.
Found: C, 65.34; H, 5.59; N, 20.60.

C. 6-(7,10-Dichloro-3,4-dihydrobenzo[b][1,6]naphthyridin-2(1H)-yl)-3-pyridine-carbonitrile, hemihydrate To a slurry of 11.5 g (0.067 mol) of 2-amino-4-chlorobenzoic acid and 120 ml of phosphorous oxychloride is added portionwise 13.5 g (0.067 mol) of the compound of B, above. The mixture is stirred under reflux for 3 hours and concentrated in vacuo. The residue is taken up in chloroform and poured carefully into a mixture of ice-NH$_4$OH and stirred for 30 minutes before extraction with chloroform. The combined extracts are washed with brine, dried over Na$_2$SO$_4$, and concentrated in vacuo. The resultant solid is triturated in ether and dried under vacuum to yield 19.9 g of title compound; m.p. 171°–173° C. (yield 84%). IR (KBr) 2205, 1600, 1540, 1500 and 1420 cm$^{-1}$; NMR (DMSO-d$_6$)δ 8.50–7.40 (complex-m, 5H), 6.77 (d, 1H), 5.05 (s, 2H), 4.10 (t, 2H), and 3.30 (t, 2H).

Analysis for: C$_{18}$H$_{12}$Cl$_2$N$_4$.½H$_2$O:
Calculated: C, 59.35; H, 3.60; N, 15.38.
Found: C, 59.50; H, 3.66; N, 15.31.

EXAMPLE 5
7-Chloro-1,2,3,4-tetrahydro-10-(2-phenylhydrazino)-2-(2-pyrazinyl)benzo[b][1,6]naphthyridine A solution of 1.5 g (4.53 mmol) of the compound of Example 2, 0.98 ml (9.96 mmol) of phenylhydrazine, 0.75 ml of concentrated hydrochloric acid, and 30 ml of absolute ethanol is stirred at reflux temperature for 6 hours. On cooling, the resulting precipitate is collected, then dissolved in methanol. Treatment of this solution with Na$_2$CO$_3$ solution results in the formation of a precipitate. The solid is collected and recrystallized from benzene-hexane to afford 0.788 g (43%) of title compound as a brown solid, m.p. 183°–186° C. (dec.); IR (KBr) 3250, 1602 and 1480 cm$^{-1}$; NMR (DMSO-d$_6$) δ8.70 (m, 2H), 8.37 (d, 2H), 8.15 (s, 1H), 7.86 (m, 1H), 7.43 (m, 1H), 7.24 (m, 2H), 6.92–6.74 (m, 3H), 4.90 (s, 2H), 4.01 (m, 2H), 3.11 (m, 2H).

Analysis for: C$_{22}$H$_{19}$ClN$_6$:
Calculated: C, 65.58; H, 4.75; N, 20.86.
Found: C, 65.68; H, 4.80; N, 20.38.

EXAMPLE 6

The ability of the compounds of the inventions to inhibit interleukin 1 is measured by the ability of the test compounds to inhibit the IL 1-induced release of neutral protease from rabbit articular chondrocytes.

This assay is carried out as follows:

Isolation of rabbit chondrocytes:

Male New Zealand White rabbits are anesthetized with 50 mg/kg of ketamine (i.m.) and killed by an intracardiac injection of 3 mls. of Nembutal. The knee joints of both legs are resected and the articular surfaces are exposed. Cartilage slices are obtained using a scalpel and are placed in a tissue culture dish (100 mm diameter) containing 10 mls of Hank's balanced salt solution (HBSS). The chondrocytes within the cartilage slices are then liberated by a series of enzyme digestions. The slices are incubated for 10 min. at 37° C. in 0.05% hyaluronidase (Sigma H-3884), rinsed with HBSS and incubated with 0.2% trypsin (Sigma T-2395) for 10 min. at 37° C. The slices are rinsed again and incubated for 10 mins. at 37° C. with 1.2% collagenase (Sigma C-5138). The slices are then rinsed again with HBSS and resuspended in 10 ml of Ham's F-12 medium containing 10% fetal bovine calf serum (FCS) and 0.2% collagenase and incubated overnight at 37° C. in a 5% CO₂ incubator. The next day, the medium containing the digested cartilage fragments and liberated chondrocytes is transferred to a 15 ml centrifuge tube and the cells are collected by centrifugation and washed twice and resuspended in Ham's F-12 medium. The cells are then plated into 24-well tissue culture plates (2×10⁵ cells/well) and incubated at 37° C. until confluent (usually 4-6 days).

Stimulation of chondrocytes and drug treatment:

The confluent chondrocytes are rinsed twice with serum-free Ham's F-12 medium and 1 ml is added to each well. Fifty $1 of purified human IL 1(100 Units/ml; Genzyme Corporation, Boston, MA) is then added to stimulate these cells to secrete neutral protease. To measure drug effects, the cells are treated with test compound 10 min. prior to addition of IL 1. The standard screening dose is 10 $M. Twenty-four hours after IL 1 stimulation, supernatant fluids are collected and assayed for neutral protease activity.

Neutral protease assay:

The neutral protease activity of chondrocyte supernatant fluids is determined by their ability to degrade an insoluble protease substrate, azocoll (Sigma). Supernatants are treated for 10 min. at room temperature with 350 $M p-aminophenyl-murcuric acetate to activate the latent enzyme. Three hundred $1 of supernatant is then mixed with 500 $1 of a 20 mg/ml suspension of azocoll and incubated at 37° C. for 18-24 hrs. with gentle rocking. The mixtures are centrifuged and the amount of substrate hydrolyzed is determined by measuring the absorbance of the supernatant at 520 nm.

Drug effects are calculated as the % change in enzyme activity (absorbance) by supernatants from drug-treated chondrocytes relative to enzyme activity of supernatants from vehicle-treated chondrocytes as follows:

$$\frac{(A_{520}) \text{ Untreated Supernatant} - A_{520} \text{ Drug Treated Supernatant}}{A_{520} \text{ Untreated Supernatant}} (\times 100)$$

Where tested in this assay, the compounds of the invention gave the following results:

| Compound of Example No. | Dose (μM) | % Inhibition (I.S.D.) |
|---|---|---|
| 1 | 10 | 34 ± 8 |
| 3 | 10 | ≦20 |
| 4 | 10 | 94 |
| 5 | 10 | 83 |
| 5 | 10 | 85 ± 5 |

The results show that the compounds tested exhibit a moderate to very significant inhibition of IL 1-induced protease secretion.

What is claimed is:

1. A compound having the formula

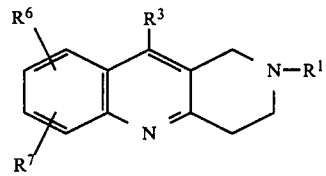

wherein
R¹ is pyridyl, quinolinyl, pyrazinyl, pyridazinyl, pyrimidinyl, quinoxalinyl, quinazolinyl or any of the foregoing substituted with halo, lower alkyl, lower alkyl carbonyl, benzoyl, carboxy, lower alkoxycarbonyl, OR², N(R²)₂, CON(R²)₂, SO₃R², SO₂N(R²)², phenylsulfonyl, lower alklysulfonyl, cyano, nitro or trifluoromethyl;
R² is hydrogen, lower alkyl or phenyl;
R³ is halo, morpholino, 4-methylpiperazino, R⁴NNHR⁵, NR⁴R⁵, OR⁵, SR⁵, R⁴NCH₂CH₂OCH₃, SCH₂CH₂CH₂NH₂ or

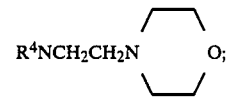

R⁴ is hydrogen or lower alkyl;
R⁵ is hydrogen, lower alkyl, lower alkanoyl, lower cycloalkyl or phenyl; and
R⁶ and R⁷ are each independently, hydrogen, halo, nitro, lower alkoxy, lower alkyl, cyano, trifluoromethyl, phenyl, carboxy or lower alkoxycarbonyl.

2. The compound of claim 1, having the name 7,10-dichloro-1,2,3,4-tetrahydro-2-(2-pyrimidinyl)benzo[b][1,6]naphthyridine.

3. The compound of claim 1, having the name 7,10-dichloro-1,2,3,4-tetrahydro-2-(2-quinolinyl)benzo[b][1,6]naphthyridine.

4. The compound of claim 1, having the name 6-(7,10-dichloro-3,4-dihydrobenzo[b][1,6]naphthyridin-2(1H)-yl)-3-pyridinecarbonitrile.

5. The compound of claim 1, having the name 7-chloro-1,2,3,4-tetrahydro-10-(2-phenylhydrazino-2-(2-pyrazinyl) benzo[b][1,6]naphthyridine.

* * * * *